(12) United States Patent
Riley et al.

(10) Patent No.: US 9,808,011 B2
(45) Date of Patent: Nov. 7, 2017

(54) PENTACYCLIC TRITERPENE COMPOUNDS AND USES THEREOF

(71) Applicant: BioVectra Inc., Charlottetown (CA)

(72) Inventors: John G. Riley, Crapaud (CA); Richard J. Bethell, Charlottetown (CA)

(73) Assignee: BIOVECTRA INC., Charlottetown (CA)

( * ) Notice: Subject to any disclaimer, the term of this patent is extended or adjusted under 35 U.S.C. 154(b) by 128 days.

(21) Appl. No.: 14/570,333

(22) Filed: Dec. 15, 2014

(65) Prior Publication Data

US 2016/0165892 A1 Jun. 16, 2016

(51) Int. Cl.
*A01N 45/00* (2006.01)
*C07J 63/00* (2006.01)

(52) U.S. Cl.
CPC ............ *A01N 45/00* (2013.01); *C07J 63/008* (2013.01)

(58) Field of Classification Search
CPC .............................. A01N 45/00; C07J 63/008
See application file for complete search history.

(56) References Cited

U.S. PATENT DOCUMENTS

| | | | |
|---|---|---|---|
| 5,750,578 A | 5/1998 | Carlson et al. | |
| 5,869,535 A | 2/1999 | Pezzuto et al. | |
| 5,962,527 A | 10/1999 | Pezzuto et al. | |
| 6,048,847 A | 4/2000 | Ramadoss et al. | |
| 6,214,814 B1 | 4/2001 | Ramadoss et al. | |
| 6,228,850 B1 | 5/2001 | Jaggi et al. | |
| 6,403,816 B1 | 6/2002 | Jaggi et al. | |
| 6,458,834 B2 | 10/2002 | Glinski et al. | |
| 6,642,217 B2 | 11/2003 | Krasutsky et al. | |
| 6,890,533 B2 | 5/2005 | Bomshteyn et al. | |
| 7,144,875 B2 | 12/2006 | Gibson et al. | |
| 8,278,068 B2 | 10/2012 | Vielhaber et al. | |
| 2002/0068098 A1 | 6/2002 | Babish et al. | |
| 2002/0091091 A1 | 7/2002 | Burman et al. | |
| 2002/0099164 A1 | 7/2002 | Watterson et al. | |
| 2005/0014730 A1 | 1/2005 | Carlson et al. | |
| 2006/0252733 A1 | 11/2006 | Jansen | |
| 2009/0136521 A1 | 5/2009 | Parmar et al. | |
| 2009/0136566 A1 | 5/2009 | Krasutsky et al. | |
| 2009/0298113 A1 | 12/2009 | Vielhaber et al. | |
| 2010/0080761 A1 | 4/2010 | Herrmann et al. | |
| 2010/0143267 A1 | 6/2010 | Pertile et al. | |

FOREIGN PATENT DOCUMENTS

| | | |
|---|---|---|
| CA | 2515384 A1 | 8/2004 |
| DE | 19854402 A1 | 5/2000 |
| EP | 0943620 A2 | 9/1999 |
| EP | 2288375 B1 | 4/2012 |
| JP | 9-067249 | 3/1997 |
| JP | 9-087156 | 3/1997 |
| JP | 9-143050 | 6/1997 |
| JP | 10-265328 A | 10/1998 |
| JP | 11-293300 | 10/1999 |
| JP | 2001-163758 | 6/2001 |
| RU | 2411934 C1 | 2/2011 |
| WO | 9504526 A1 | 2/1995 |
| WO | 9629068 | 9/1996 |
| WO | 9916449 | 4/1999 |
| WO | 9947113 | 9/1999 |
| WO | 0003748 | 1/2000 |
| WO | 0003749 | 1/2000 |
| WO | 0209698 A1 | 2/2002 |
| WO | 0209720 A1 | 2/2002 |
| WO | 0226761 | 4/2002 |
| WO | 2008054585 A2 | 5/2008 |
| WO | 2010114305 | 10/2010 |
| WO | 2011003886 A1 | 1/2011 |

OTHER PUBLICATIONS

Kazakova et al., "Synthesis and Modification of Triterpenoids with Two Lupan Backbones", Russian J. of Bioorganic Chemistry, vol. 35(5), pp. 645-650, 2009.*
Yu et al., "Development of bivalent oleanane-type triterpenes as potent HCV entry inhibitors", European J. of Medicinal Chemistry, vol. 77, pp. 258-268, 2014.*
Yogeeswari et al., "Betulinic Acid and Its Derivatives: A Review on their Biological Properties", Current Medicinal Chemistry, Mar. 1, 2005, 12, pp. 657-666.
Jeromenok, "Polymers from the Natural Product Betulin; A Microstructural Investigation", Published by: Institutional Repository of the University of Potsdam Mar. 12, 2012, pp. 94-96.
Kling, "PEGylation of Biologics", http://www.bioprocessintl.com/upstream-processing/biochemicals-raw-materials/pegylation-of-biologics-340623/, Mar. 1, 2013, 13 pages.
Roberts et al., "Chemistry for peptide and protein PEGylation", Advanced Drug Delivery Reviews, vol. 54, accepted for publication Jan. 22, 2002, published 2002, pp. 459-476.
Tolstikov et al., "Betulin and Its Derivatives. Chemistry and Biological Activity", Chemistry for Sustainable Development, vol. 13, received for publication May 25, 2004, published 2005, pp. 1-29.

* cited by examiner

*Primary Examiner* — Barbara P Badio
(74) *Attorney, Agent, or Firm* — Broden Ladner Gervais LLP; Kathleen E. Marsman

(57) ABSTRACT

Disclosed herein is a PEGylated bis pentacyclic triterpene, compositions comprising the PEGylated bis pentacyclic triterpene, methods of preparing the PEGylated bis pentacyclic triterpene, and a method of treating or preventing a fungal disease in a plant using the compounds and compositions disclosed herein. The PEGylated bis pentacyclic triterpene has the formula A-P-B, wherein A is a first pentacyclic triterpene; B is a second pentacyclic triterpene; and P is a polyethylene glycol (PEG) molecule.

14 Claims, 4 Drawing Sheets

PENTACYCLIC TRITERPENE COMPOUNDS AND USES THEREOF

FIELD

The present disclosure relates generally to compounds comprising a pentacyclic triterpene, for use in preventing or treating fungal diseases in plants.

BACKGROUND

Fungal and fungal-like pathogens are the cause of many common plant diseases and result in losses in agricultural yield, quality and profit. Blight is an example of a plant disease that is caused by fungal or fungal-like organisms and is one of the most destructive disease of potato in Canada and worldwide.

Current agents or fungicides used to treat fungal infections include polyene antibiotics, synthetic azoles and griseofulvin. Repeated use of such fungicides results in the development of resistance by the pathogen. When fungicide resistance develops, the product or other chemically similar products no longer controls the disease effectively. Thus, new, low-toxic fungicides belonging to different chemical groups are needed to maintain control of damaging diseases caused by fungi and fungal-like organisms.

Pentacyclic triterpences such as Betulin (lup-20(29)-ene-3β,28-diol), Betulinic acid and lupeol (3β, 13ξ)-Lup-20(29)-en-3-ol) are abundant, naturally occurring triterpenes that can be isolated from plants such as white birch bark. Extracts from white birch bark have been used to treat inflammations, hepatitis, lymphatic disorders, tuberculosis cancers, and skin irritations. Moreover, pentacyclic triterpenes have been shown to have anti-viral activity against herpes simplex virus (U.S. Pat. No. 5,750,578) and to have anti-bacterial and anti-fungal activity. For example, WO 02/26761 A1 discloses the use of betulin and its derivatives as an anti-fungal agent against human pathogenic fungi *Microsporum canis, Microsporum audoinii, Trichophyton mentagrophytes, Epidermophyton floccosum* in in vitro growth inhibition assays performed on agar slants and in liquid cultures.

U.S. Pat. No. 6,458,834 discloses compositions comprising pentacyclic triterpenes including ursolic acid, betulin and betulinic acid for use against the plant pathogenic fungi *Phytopthora infestans, Alternaria solani, Botrytis cinerea* and *Cersospora arachidola*.

Currently, there is a need for new anti-fungal compositions that include pentacyclic triterpenes. A need particularly exists for compositions that are effective against blight.

SUMMARY

It is an object of the present disclosure to obviate or mitigate at least one disadvantage of previous antifungal compositions comprising pentacyclic triterpenes.

Disclosed herein is a PEGylated bis pentacyclic triterpene having the formula: A-P-B, wherein A is a first pentacyclic triterpene; B is a second pentacyclic triterpene; and P is a polyethylene glycol (PEG) molecule, for use in preventing or treating a fungal disease in a plant.

In an embodiment, the first and second pentacyclic triterpenes are each independently betulin, betulinic acid, lupeol, or an analogue or derivative thereof. For example, the first and second pentacyclic triterpene may each be betulin.

Also disclosed herein is a fungicidal composition comprising the PEGylated bis pentacyclic triterpene described herein, and an agriculturally acceptable diluent.

Also described herein is a method of treating or preventing a fungal disease in a plant comprising: applying to the plant, to a soil supporting the plant, or to both the plant and the soil supporting the plant, a composition comprising a PEGylated bis pentacyclic triterpene having the formula: A-P-B, wherein A is a first pentacyclic triterpene; B is a second pentacyclic triterpene; and P is a polyethylene glycol (PEG) molecule; and an agriculturally acceptable diluent.

Also described herein is a method of preparing a PEGylated bis pentacyclic triterpene, the method comprising: combining a polyethylene glycol (PEG) molecule with an organic solvent to form a mixture; heating the mixture to reflux; removing the distillate formed in the heating step from the mixture; adding two stoichiometric equivalents of a pentacyclic triterpene with respect to the PEG molecule, a condensing agent, and, optionally, an acyl transfer catalyst to the mixture; stirring the mixture; cooling the mixture; and drying the mixture. The pentacyclic triterpene may be betulin, betulinic acid, lupeol, or an analogue or derivative thereof. The organic solvent may be toluene. The condensing agent may be N,N'-diisopropylcarbodiimide (DIC), and the acyl transfer catalyst, if required, may be dimethylaminopyridine (DMAP).

Also disclosed is a PEGylated bis pentacyclic triterpene prepared by this method, and the use of the compound so prepared for preventing or treating a fungal disease in a plant by applying the compound to the plant, to a soil supporting the plant, or to both the plant and the soil supporting the plant.

Other aspects and features will become apparent to those ordinarily skilled in the art upon review of the following description of specific embodiments in conjunction with the accompanying figures.

BRIEF DESCRIPTION OF THE DRAWINGS

Embodiments of the present disclosure will now be described, by way of example only, with reference to the attached Figures.

DETAILED DESCRIPTION

Figure 1:
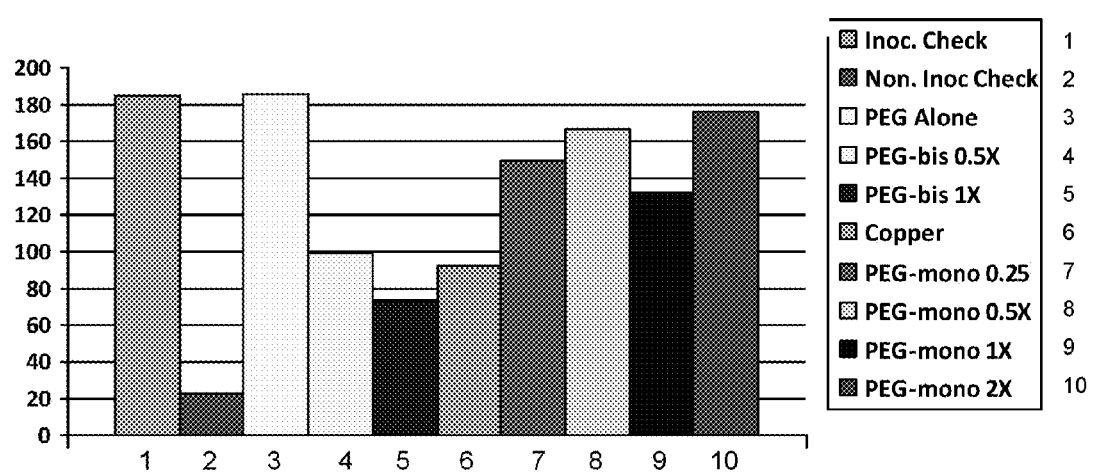
FIG. 1 is a graph showing the mean number of late blight lesions per plant (AUDPC).

Pentacyclic triterpenes such as betulin and its analogues and derivatives are hydrophobic compounds and are poorly soluble in water. Because of their low water solubility, the handling and administration of pentacyclic triterpenes is difficult as they are difficult to apply to crops in non-emulsion formulations. As a result, the use of betulin and its analogues and derivatives as antifungal agents has been limited.

One strategy for increasing the solubility of water insoluble compounds is to make conjugates of a pro-drug with a high molecular weight polyethylene glycol (PEG) molecule. Various in vivo experiments have established that the molecular weight of PEG for these types of pro-drugs must be greater than 40 kDa in order to maintain an adequate resident circulation time and allow for an efficacious therapeutic effect.

The inventors have identified that the use of high molecular weight PEGs (>40 KDa) to produce water soluble pro-drugs is not necessary for agricultural efficacy and that pentacyclic triterpenes that are slightly soluble are more effective at treating or preventing fungal infections. The inventors have surprisingly found that PEGylated bis pentacyclic triterpenes are more effective as anti-fungal agents than PEGylated mono bis pentacyclic triterpenes. Without being bound by theory, it is believed that high solubility does not necessarily correlate with high activity with respect to PEGylated bis pentacyclic triterpenes, such as, for example, PEGylated bis betulin.

Generally, the present disclosure provides compounds and compositions that are useful in preventing or treating fungal diseases in plants. Specifically, the disclosed compounds are PEGylated bis pentacyclic triterpenes having the formula:

A-P-B wherein, A and B are each independently pentacyclic triterpenes and P is a polyethylene glycol (PEG) molecule that forms a covalent bond with A and B.

The compositions disclosed herein comprise compounds of the formula A-P-B and an agriculturally acceptable diluent.

The term "pentacyclic triterpenes" is meant to describe members of the terpene family that consist of six isoprene units (arranged in 5 rings) and have the molecular formula $C_{30}H_{48}$. Pentacyclic triterpenes are easily isolable compounds and are usually concentrated in the outermost layers of a plant such as the plant cuticle, fruit peel or bark. Terpenes are a large and diverse class of organic compounds, produced by a variety of plants, particularly conifers and are derived biosynthetically from units of isoprene, which have the molecular formula $C_5H_8$ and are classified by the number of isoprene units in the molecule. Advantageously, the anti-fungal compounds and compositions disclosed herein are not very expensive to manufacture as they are easily extracted from abundant natural products or are easily synthesized.

Pentacyclic triterpenes can be classified into many subgroups including lupane, oleanane, gammacerane, hopane or ursane groups based on their carbon skeleton. Lupanes have the following general structure:

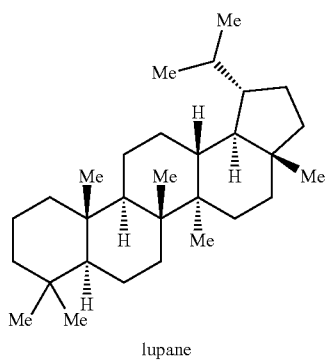

lupane

In some embodiments, the pentacyclic triterpenes are members of the lupane group. Members of the lupane group include, but are not limited to, lupenone, lupeol, betulin, betulinic acid, and tiarellic acid. Lupanes have been extensively studied as a natural source of therapeutics. Most lupane-type terpenoids cholesterol-like triterpenoids are virtually insoluble in water and exhibit poor phamacogenic properties.

Betulin

Betulin, which is also known as lup-20(29)-ene-3β,diol, has the molecular formula $C_{30}H_{50}O_2$ and is an abundant, naturally occurring triterpene of lupane structure. It has a pentacyclic ring structure, and hydroxyl groups in positions C3 and C28. Betulin is commonly isolated from the bark of birch trees and forms up to 30% of the dry weight of the extractive.

Betulinic Acid (3β-hydroxy-lup-20(29)-en-28-oiacid) is a pentacyclic triterpene isolated from various plants including, for example, *Quisqualis fructus, Coussarea paniculata, Caesalpinia paraguariensis, Vitex negundo, Ilex macropoda* (Togeeswari and Sriram, Current Medicial Chemistry, 2005, 12, 657-666).

Lupeol is a pharmacologically active triterpenoid having the formula (3β,13ξ)-Lup-20(29)-en-3-ol. The chemical structures of Betulin, Betulinic Acid and Lupeol are as follows:

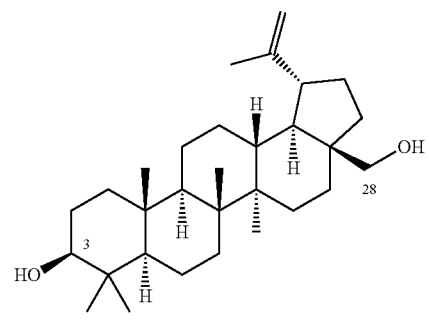

Betulin

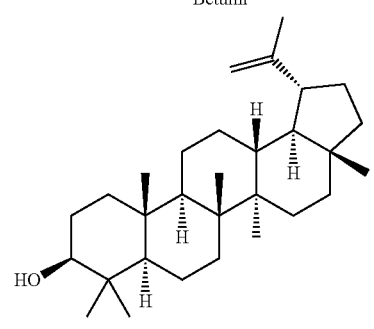

Lupeol

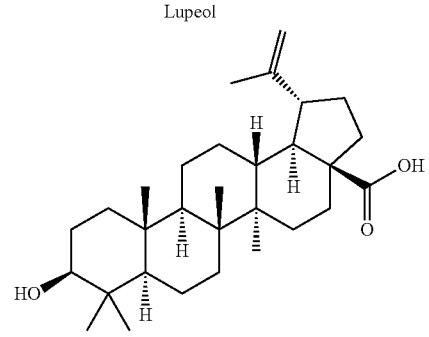

Betulinic Acid

The term "derivative", when used in association with pentacyclic triterpenes, i.e. "pentacyclic triterpene derivative", or any examples of pentacyclic triterpenes such as "betulin derivatives", or "betulinic acid derivatives" refers to a compound that is derived from the pentacyclic triterpene by a chemical or physical process. For example, pentacyclic triterpene derivatives refer to pentacyclic triterpene compounds in which the substituents on the A-, B-, C- and D-rings are modified in a way well known to a person skilled in the art.

Suitable betulin derivatives, betulinic acid derivatives, and related (steroid-like) compounds would be known to a person of skill in the art, and include such compounds as can be found, for example, in the following documents, the contents of which are incorporated herein by reference:

WO 02/26761
Yogeeswari and Sriram, 2005, Current Medicinal Chemistry, 12, 657-666
U.S. Pat. No. 6,458,834
U.S. Pat. No. 6,403,816
U.S. Pat. Pubn Appln. 20060252733 A1
U.S. Pat. No. 6,228,850
U.S. Pat. No. 5,962,527
U.S. Pat. No. 5,869,535
U.S. Pat. No. 6,214,814
U.S. Pat. No. 6,048,847
US Pubn. Appln. 2002068098
US Pubn. Appln. 2002099164
US Publn. Appln. 2002091091
CA 2515384
DE 19854402
EP 22-1999092
JP 19-19970603
JP 17-20010619
JP 12-19970331
JP 7-19991026
JP 13-19981006
JP 7-19970311
WO 95/04526
WO 0209698
WO 99/47113
WO 99/16449
WO 00/03749
WO 00/03748
WO 02/09720 and
WO 96/29068.

By "substituent" it is meant an atom or group of atoms substituted in place of a hydrogen atom on the parent chain of a hydrocarbon. The terms substituent, side-chain, group, branch, or pendant group are used almost interchangeably to describe branches from a parent structure. Combinations of substituents are permissible only if such combinations result in stable compounds.

The term "analogue" refers to a compound having similar chemical properties to the referenced compound.

The term "PEGylation" is meant to refer to the act of covalently coupling a PEG molecule to a compound, for example, a pentacyclic triterpene, which is then referred to as a PEGylated pentacyclic triterpene. The compounds described herein are "bis" pentacyclic triterpenes. As used herein, the term "bis" refers to two pentacyclic triterpenes conjugated to a single PEG molecule. To couple a PEG to two pentacyclic triterpenes it is necessary to activate the PEG by preparing a derivative of the PEG having a functional group at at least two termini. In general, a functional group is chosen based on the type of available active group on the molecule to which it is to be coupled. A PEG molecule may be coupled to a betulin molecule through either of its terminal hydroxyl groups. In some embodiments the linkage between the PEG molecule and a pentacyclic triterpene may be a carboxylic ester linkage. However, a person of skill in the art would understand that other linkages are possible. For example, the alcohol of a pentacyclic triterpene could by conjugated to PEG via a carbonate linkage (OCOOPEG), a carbamate linkage (OCONHPEG), or a phosphate ester linkage. Techniques used to activate PEGs and form PEG derivatives would be known to a person of skill in the art.

In embodiments wherein the pentacyclic triterpene is Betulinic acid, an acid on the PEG molecule must be activated before coupling to the Betulinic Acid. Acid halides or esters of N-hydroxysuciccinimide and pentafluorophenol, or other leaving groups could be employed in this transformation. In other embodiments, the acid group of Betulinic acid may be coupled directly to the PEG via an ester bond. In a further embodiment, the linkages are the combination of various covalent bonds including, but not limited to, carboxylic ester, carbonate and carbamate. In other embodiments, the PEG molecule may be covalently bound using mixed functional linkages.

As used herein, the term "polyethylene glycol (PEG)" refers to the compound $H(OCH_2CH_2)_nOH$ which typically exists in polymer chains. PEG is also known as polyethylene oxide (PEO) or polyoxythylene (POE), depending on its molecular weight. PEGs are prepared by polymerization of ethylene oxide and are commercially available over a wide range of molecular weights from 300 g/mol to 10,000,000 g/mol. Most PEGs include molecules with a distribution of molecular weights (i.e. they are polydisperse). The size distribution can be characterized statistically by its weight average molecular weight (Mw) and its number average molecular weight (Mn), the ratio of which is called the polydispersity index (Mw/Mn). MW and Mn can be measured by mass spectrometry. As used herein, the numbers that are included in the names of PEGs indicate their average molecular weights. For example, a PEG with n=9 would have an average molecular weight of approximately 400 daltons (Da), and may be labeled PEG 400. PEG molecules can range in molecular weight from 200 Da to 40000 Da or more.

In some embodiments the PEG may have a molecular weight of about 1500 Da to about 10000 Da. In some embodiments, the PEG may have a molecular weight in the range of 1500 Da to 8000 Da. In some embodiments the PEG may have a molecular weight of 3000 Da, 4000 Da, 5000 Da, 6000 Da, 7000 Da, 8000 Da, 9000 Da or 10000 Da. In an embodiment, the PEG has a molecular weight of about 3000 Da. In a further embodiment, the PEG has a molecular weight of about 4000 Da.

The PEG molecules disclosed herein are capable of binding at least two pentacyclic triterpene molecules. The PEG molecule may be capable of binding more than two pentacyclic triterpene molecules.

In some embodiments the PEG molecules are bifunctional PEG derivatives. As used herein the term "bifunctional PEG derivatives" refers to a PEG molecule that has been functionalized with a reactive moiety at two terminals and is capable of conjugating at least two pentacyclic triterpene molecules.

In some embodiments, the PEG molecules may be homobifunctional derivatives. As used herein, the term "homobifunctional poly(ethylene glycol) (PEG)" refers to PEG derivatives that are synthetic polyethers containing two of the same type of functional groups. The functional group may be, for example, a carboxylate, a carbamate, a carbonate, an amine, an azide, an alkyne, an alkene, a sulfonyl chloride, a phosphonyl chloride, a maleimide, NHS esters, a pentafluorophenyl ester, a thioester, acrylates, methacrylates, carboxylates and thiols. Examples of homobifunctional PEG derivatives include, but are not limited to, α,ω biscarboxymethyl PEG, α,ω-Bis{2-[(3-carboxy-1-oxopropyl)amino]ethyl}polyethylene glycol, 4,7,10,13,16,19,22,25,32,35,38,41,44,47,50,53-Hexadecaoxa-28,29-dithiahexapentacontanedioic acid, O,O'-Bis(2-aminoethyl) polyethylene glycol, O,O'-Bis(2-azidoethyl)polyethylene glycol, or Poly(ethylene glycol) bis(carboxymethyl) ether.

In a preferred embodiment, the PEGylated bis pentacyclic triterpenes are esters. In an embodiment, the reactive moieties on the PEG molecule are carboxylic acid, which form an ester linkage with the OH groups present at C3 or C28 of a first pentacyclic triterpene and C3 or C28 of a second pentacyclic triterpene. In an embodiment the ester linkage is formed between the OH group present at C3 of a first pentacyclic triterpene molecule and the OH group present at C28 of a second pentacyclic triterpene molecule. In another embodiment the ester linkage is formed between the OH group present at C3 of a first pentacyclic triterpene molecule and the OH group present at C3 of a second pentacyclic triterpene molecule. In yet another embodiment the ester linkage is formed between the OH group present at C28 of a first pentacyclic triterpene molecule and the OH group present at C3 of a second pentacyclic triterpene molecule. In a further embodiment the ester linkage is formed between the OH group present at C28 of a first pentacyclic triterpene molecule and the OH group present at C28 of a second pentacyclic triterpene molecule. In an embodiment, the PEGylated bis pentacyclic triterpenes esters are PEGylated bis betulin esters.

In a preferred example, the homobifunctional PEG molecule is a polyethylene glycol bis(caboxymethyl) ether, also known as polyethylene glycol 250 diacid, having the formula $HOOCCH_2(OCH_2CH_2)_nOCH_2COOH$ and CAS ID 39927-08-7.

In some embodiments, the PEG molecules are heterobifunctional derivatives which are PEGs bearing dissimilar terminal groups. As used herein, the term "heterobifunctional poly(ethylene glycol) (PEG) derivatives" are synthetic polyethers containing two functional groups of different types.

The PEG molecules may have different geometries. For example, the PEG molecule may be linear or may be branched, multiarm, forked, or Y-shaped. Branched PEGs may have three to ten PEG chains emanating from a central core group. Star PEGs may have 10 to 100 PEG chains emanating from a central core group. Comb PEGs may have multiple PEG chains normally grafted onto a polymer backbone.

In some embodiments, the compounds and compositions disclosed herein are useful in treating or preventing a fungal disease in a plant.

As used herein, "treating" means either slowing, stopping or reversing the progression of the disease. In a preferred embodiment, "treating" means reversing the disease to the point of eliminating the disease. In some embodiments, "treating" refers to protecting uninfected tissues and new growth and does not refer to promoting sick tissues (yellow or brown leaves, rotted roots) to become healthy again.

As used herein "preventing" means either slowing, stopping or reversing a fungal disease in plants that has not yet occurred. The plant may be at risk of developing fungal disease due to growth conditions or nearby infection.

Methods are described herein for treating a plant showing symptoms of a disease or for preventing a disease in a plant that is at risk of developing a pathogenic infection. Such methods comprise administering a compound or a composition as described herein to the plant, a plant part or parts (such as, but not limited to a leaf, a stem, a trunk, or a root) or soil supporting the plant in an effective amount. The soil supporting the plant is the soil that physically supports the plant and from which the plant draws its nutrients. In some embodiments the pathogenic infection may be an infection caused by a fungal or fungal-like organism.

An "effective amount" of a PEGylated compound, with respect to the subject method of treatment, refers to an amount of the PEGylated compound, which when applied inhibits or brings about, e.g. prevents or produces changes in the rate or number symptoms of the disease according to acceptable standards for the disease to be treated or the effect desired.

The compounds and compositions disclosed herein may be delivered hourly, daily, weekly, monthly, yearly (e.g. in a time release format) or as a one-time delivery. In certain embodiments, the PEGylated compounds are administered at a dose per plant per day of at least about 0.8 g/L, in 5 doses over a period of 7 days. In certain embodiments the the PEGylated compounds may be administered at a dose per plant per day of about 0.15 g/300 mL. In other embodiments the PEGylated compounds may be administered at a dose of 0.8 g/L to about 10 g/L per plant. In further embodiments the PEGylated compounds may be administered at a range of 0.15-1.1 g/300 mL per plant. When used on a preventive basis, compounds and compositions may be used at lower rates and/or at longer intervals between applications. Conversely, when used to treat a disease the compounds and compositions may be used at higher rates and/or at shorter intervals. A person of skill in the art would understand how to modify the effective amount accordingly.

It is understood that one skilled in the art that the dose of the composition may vary depending on the plant type, the growth conditions and the type of administration. It is routine in the art to adjust the effective amount to suit the type of plant, the type of pathogen and the environmental conditions.

The term "plant pathogen" is meant to include any pathogen that can infect a plant and cause disease. The plant pathogen may be, for example, a bacteria, a fungus or a fungus-like pathogen. A fungus refers to a distinct group of eukaryotic spore-forming organisms with absorptive nutrition and lacking chlorophyll. It includes mushrooms, molds and yeasts.

Fungal or fungal-like pathogens often cause disease which exhibit "blight" as a symptom. Blight refers to a rapid and complete chlorosis, browning, then death of plant tissues such as leaves, branches, twigs, or floral organs. Accordingly, many diseases that primarily exhibit this symptom are called blights. Several notable examples of diseases that exhibit blight as a symptom are: late blight of potato, caused by the water mold *Phytophthora infestans*, Southern corn leaf blight, caused by the fungus *Cochliobolus heterostrophus*, Chestnut blight, caused by the fungus *Cryphonectria parasitica*, early blight of potato and tomato, caused by species of the ubiquitous fungal genus *Alternaria* and leaf blight of grasses. On leaf tissue, symptoms of blight include the initial appearance of lesions which rapidly engulf surrounding tissue.

Late blight attacks a wide range of potato varieties and is one of the most destructive diseases of potato in Canada and worldwide. It is caused by *Phytophthora infestans*, an oomycete (fungal-like organism). Late blight occurs in all areas of the country, but it is more severe under high and frequent rainfall, high humidity and cool to moderate temperatures. Early symptoms of late blight first appear on leaves as small, circular or irregularly shaped, dark, water-soaked lesions that can occur within 3 to 5 days of the initial infection. On petioles and stems, symptoms appear as dark, water-soaked lesions. Lesions expand as the pathogen colonizes the internal plant tissues. On mature lesions, the pathogen produces white, spore-bearing structures called sporangia on the underside of the leaf spots or on the surface of diseased stems. As the disease progresses, the entire vegetative/leafy part of the plant decays and becomes necrotic. Tubers can become infected at any stage of their development. Infected tubers exhibit sunken lesions on the surface and a reddish-brown rot is visible under the skin. Infected tubers are susceptible to secondary infection by other pathogens, such as soft rot bacteria, that result in a soft, watery decay of the tubers.

*Botrytis* blight, also known as gray mold, is a fungal disease caused by several species in the genus *Botrytis*. *Botrytis* blight causes buds and flowers to develop abnormally and turn brown. Affected parts may be covered with a gray mold following damp, cool weather. It affects the buds, flowers, leaves, and bulbs of many plants including: African violet, begonia, chrysanthemum, cyclamen, dahlia, geranium, lily, peony, rose, and tulip. *Botrytis cineria* is a necrotrophic fungus that affects many plant species including but not limited to soft fruits; grapes, strawberries, blueberries, tomatoes, and bulb crops; carrots, parsnips, beets, beans, turnips, onions and garlic. The extent and severity depends on weather conditions and cultural practices.

Blight is also a disease of turfgrass. *Microdochium nivale* (pink snow mould in turfgrass, also causes Michrodium patch), *Botrytis cinerea* (bean blight, gray mold other plants). The causative organism of these diseases. *Microdochium nivale*, was formerly known as *Fusarium nivale* and Michrodium patch is sometimes referred to as *Fusarium* patch. The compounds and compositions disclosed herein are useful in the treatment of blight.

The fungal disease may be a disease caused by a fungal pathogen selected from the group consisting of *Phytophthora infestans, Microdochium nivale*, and *Botrytis cinerea*.

Synthesis of PEGylated bis-pentacyclic triterpenes

The compounds described herein may be prepared using methods known to those of skill in the art. The following synthetic route provides one possible route for formation of a PEGylated bis pentacyclic triterpene having an ester linkage, but it is not intended as limiting, as other routes are possible.

Generally, the method involves reacting a minimum of two stoichiometric equivalents of a pentacyclic triterpene with a bifunctional PEG in a suitable organic solvent such as toluene or tetrahydrofuran, in the presence of a condensing reagent, such as N,N'-Dissopropylcarbodiimide (DIC) and, if required, an acyl transfer catalyst, such as 4-Dimethylaminopyridine (DMAP) to form a PEGylated bis pentacyclic triterpene ester.

In a preferred embodiment, the compound has the Formula I:

Formula I wherein P is a bifunctional PEG molecule. The bifunctional PEG molecule may be attached via an ester linkage at positions C3 or C28 of a first betulin molecule and C3 or C28 of a second betulin molecule.

The compounds and compositions disclosed herein may be formulated as a sprayable formulation, a wettable powder, a flowable, a dry flowable, a water-dispersible granule, or an emulsifiable concentrate. However, these formulations are not limiting and a person of skill in the art would understand how to formulate the compounds and compositions disclosed herein for application to plants.

The PEGylated bis pentacyclic triterpene esters disclosed herein may be used in combination with known fungicidal products in the same formulation. Appropriate fungicides would be known to a person of skill in the art. For example, the PEGylated bis pentacyclic triterpene esters disclosed herein may be prepared in prepackaged mixtures containing two or more active ingredients. Mixtures may provide protection against fungicide resistance and may provide a broader spectrum of activity against fungal plant diseases. Also, improved disease control (synergism) may occur with mixtures of fungicides. Prepackaged mixtures offer convenience and assurance against incompatibility.

In an embodiment, the PEGylated bis pentacyclic triterpenes disclosed herein may be used in combination with mono PEGylated pentacyclic triterpenes. Formulations comprising PEG Betulin mono ester with PEG Bis betulin ester produce a mixture with increased amounts of the active (PEGylated bis betulin) form when compared to formulations comprising PEG Bis betulin ester alone.

Example 1

Synthesis of PEG Betulin Mono Ester Analogues

Three derivatives of PEG Betulin Mono Ester were prepared. The first two derivatives were synthesized by esterifying the free carboxylate of PEG Betulin Mono Ester with either ethanol or octanol (Scheme 1.) The third derivative was prepared from carboxylmethyl MPEG 3,000 Da (Scheme 2.) to produce an MPEG Betulin Ester. In this derivative the free carboxylic acid group of PEG Betulin mono ester is replaced with a methyl ether.

Scheme 1. Synthesis of PEG Betulin Ethyl and Octyl Ester derivatives

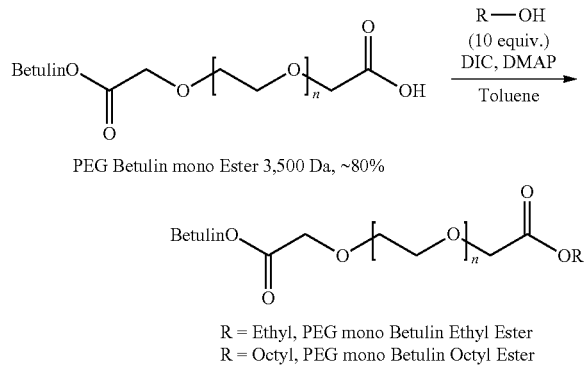

Scheme 2. Synthesis of MPEG Betulin Ester 3,500 Da

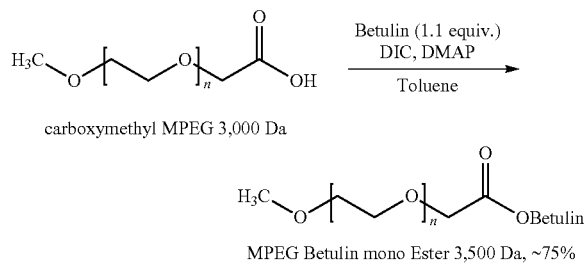

PEG Betulin Mono Ester 3,500 Da (10 g) was combined with toluene (150 mL) and heated to reflux. The distillate (50 mL) was removed via a dean stark trap and the mixture was then cooled to 30° C. To the mixture was then added DMAP (203 mg, 0.5 equiv.) followed by octanol (4.6 mL, 10 equiv) and DIC (0.57 mL, 1.0 equiv.). The mixture was then stirred for 2 hours and isolated by pouring the mixture into stirring MTBE (500 mL). After cooling in an ice bath the solid was collected, bulk washed with isopropyl alcohol for 1 hour, then collected and dried. Yield: 7.9 g.

Example 2

Solubility of PEG Betulin Esters in Aqueous Solution

The aqueous solubility of the PEG betulin derivate esters produced in EXAMPLE 1 in aqueous solution was then determined. The results of this testing is shown in Table 1.

TABLE 1

Solubility of PEG Betulin Esters in aqueous solution.

| Compound | Aqueous solubility (g/L) |
| --- | --- |
| PEG Betulin Monoester | >400 |
| PEG Mono Betulin Ethyl Ester | >400 |
| PEG Mono Betulin Octyl Ester | >300 |
| MPEG Betulin Ester | >400 |

The results in Table 1 show that the presence of the free carboxylic acid group in PEG Betulin Mono Ester does not impart a significant aqueous solubility when compared to other derivatives. Materials bearing either an ethyl or octyl ester at the other end of the polymer, as well as a methyl ether, exhibited similar high aqueous solubility.

Example 3

Synthesis of PEG Bis-Betulin Ester 4,000 Da and PEG Bis-Betulin Ester 7,000 Da

PEG bis-betulin ester 4000 Da was prepared according to Scheme 3:

Scheme 3. Synthesis of PEG bis-Betulin Ester 4,000 Da

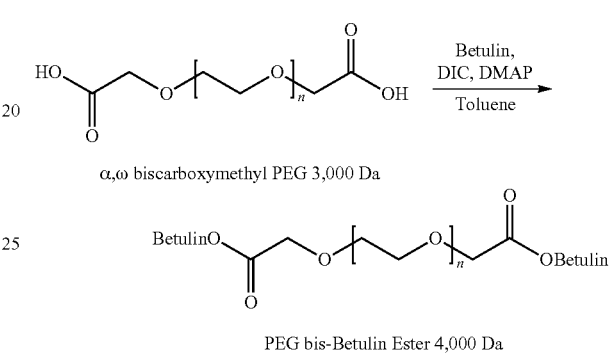

PEG bis betulin ester 4,000 Da was prepared using PEG Bis-acid 3,000 Da. PEG Bis-Acid 3,000 Da (20 g) was combined with toluene (600 mL) and heated to reflux. The distillate (100 mL) was removed via a dean stark trap and the mixture was then cooled to 50° C. To the mixture was then added DMAP (407 mg, 0.5 equiv.) followed by Betulin (3.24 g, 1.1 equiv) and DIC (1.03 mL, 1.0 equiv.). The mixture was then stirred for 2 hours and isolated by pouring the mixture into stirring MTBE (1.0 L). After cooling in an ice bath the solid was collected and dried. Yield: 21.1 g.

Example 4

Solubility of PEG Betulin Esters in Aqueous Solution at Ambient Temperature and in Octanol at 37° C.

The aqueous solubility of PEG Betulin derivative esters produced in EXAMPLEs 1 and 3 was determined at ambient temperature, while the solubility in octanol was determined at 37° C. Table 2 shows the solubility of PEG betulin esters in aqueous solution at ambient temperature and in octanol at 37° C.

TABLE 2

Solubility of PEG Betulin Esters

| Compound | Molecular Weight Of Compound | Aqueous solubility at Ambient (g/L) | Octanol solubility at 37° C. (g/L) |
| --- | --- | --- | --- |
| PEG Betulin Monoester | 3,500 Da | >400 | ~20 |
| PEG Bis Betulin Ester | 4,000 Da | ~1.6 | >400 |
| PEG Mono Betulin Ethyl Ester | 3,500 Da | >400 | ~250 |
| PEG Mono Betulin Octyl Ester | 3,500 Da | >300 | >300 |
| MPEG Betulin Ester | 3,500 Da | >400 | ~8 g/L |
| PEG Betulin Monoester | 10,500 Da | >400 | <10 |
| PEG Bis Betulin Ester | 7,000 Da | ~2.4 | NA |
| PEG Bis Betulin Ester | 11,000 Da | >400 | <10 |

The solubility of PEG Betulin Mono Ester 3,500 Da in water was found to be significantly higher than that of PEG bis-Betulin Ester. An upper solubility limit was not determined during testing, however miscibility was observed at up to 400 g/L or about 50 g of dissolved Betulin/L of aqueous solution. A usable solution of PEG Betulin Mono Ester was determined to be approximately 200 g/L or about 25 g of dissolved Betulin/L of aqueous solution.

In addition to the significant increase in solubility of the mono-PEGylated Betulin, the synthesis of this compound produced a mixture that was highly enriched in mono-PEGylated Betulin (77%) with surprisingly low levels of PEG bis-Betulin Ester. A further investigation identified reaction temperature as a critical process parameter for increasing the selectivity of this reaction, producing materials with up to 80% PEG Betulin Mono Ester containing as low as 4% PEG bis-Betulin Ester. These results indicate the chemistry used to prepare these PEGylated Betulin derivatives is remarkably selective towards the formation of PEG Betulin Mono Ester and produces products that have a high solubility in aqueous solution.

In general, materials that exhibit high aqueous solubility showed poor solubility in warm octanol. PEG Bis Betulin Ester, which is slightly soluble in water, was found to be very soluble in warm octanol. Interestingly, both PEG Mono Betulin Ethyl and Octyl esters showed good solubility in both water and warm octanol, with the Octyl ester having measurably higher octanol solubility than the Ethyl ester.

Example 5

Solubility of PEG Betulin Esters Mixed in Various Ratios

Various amounts of PEG Betulin monoester and PEG Bis Betulin ester were combined in dichloromethane and stirred until dissolved. The products were then precipitated with MTBE, collected and dried.

The aqueous solubility of each mixture was then determined at ambient temperature and the relative amounts of each component was then calculated. Results are tabulated in Table 3.

TABLE 3

Solubility of PEG Betulin Esters mixed in various ratios

| Ratio of Mono:Bis | Solubility of Mixture (g/L) | Mono Dissolved (g/L) | Bis Dissolved (g/L) |
| --- | --- | --- | --- |
| 100:0 | >400 | >400 | 0 |
| 0:100 | ~1.6 | 0 | ~1.6 |
| 1:1 | 45 | 22.5 | 22.5 |
| 3:1 | 90 | 67.5 | 22.5 |
| 9:1 | 175 | 157.5 | 17.5 |

The results in table 3 indicate the mixing PEG Bis Betulin Ester with PEG Betulin mono Ester can improve the overall solubility of PEG Bis Betulin ester. These findings indicate that a formulation with a higher dosage of PEG Bis Betulin Ester can be prepared. In some embodiments the formulation of PEG Betulin mono ester with the PEG Bis betulin ester could produce a mixture with up to 10× the amount of the active form when compared to formulating PEG Bis betulin ester alone. A higher dose/L could be applied to a plant when such mixtures are prepared.

Example 6

Efficacy of PEG-BETULIN for Control of Late Blight of Potato and Crop Tolerance, Under Greenhouse Conditions.

In this example, weekly applications of PEG bis-betulin and PEG-mono-betulin at various concentrations were assessed for control of *Phytophthora infestans* on the susceptible potato cultivar 'Colomba' compared to a commercial standard fungicide Copper Spray 50W (copper oxychloride), an inoculated (water) check and a non-inoculated (healthy) check. The trial was conducted in winter in a research greenhouse.

It was postulated that a more soluble form of PEGylated Betulin would allow for a higher dose of antifungal agent per unit of applied solution and thusly produce greater antifungal activity. In order to investigate this hypothesis, a mono-PEGylated form of Betulin was prepared by using only one stoichiometric equivalent of Betulin during the coupling reaction with PEG bis-Acid (Scheme 2.).

Materials:

PEG (polyethylene glycol), PEG-bis-betulin ester (4.0 kDa) as prepared in Scheme 3, PEG-mono-BETULIN (3.5 kDa) as prepared in Scheme 1, COPPER SPRAY 50W (copper oxychloride, 50%).

Methodology:

The trial was conducted in a designated research poly greenhouse at Kwantlen Polytechnic University, Langley, BC, from December to March. On December 23, 100×2-gallon pots were washed with dish soap and sanitized by dipping in CHEMPROCIDE (7.5% DDAC) at 10 mL/L for 5 minutes. The potting medium consisted of 2/3 Sunshine Mix #4 and 1/3 coarse perlite. The greenhouse had supplemental light and heat. An overhead misting system was set up to provide irrigation and the research bench was covered with an irrigation capillary mat throughout the trial period, to maintain high humidity for infection and disease development.

The potatoes were seeded on December 30, in a moist potting mixture to which a slow release (6-month) granular fertilizer containing micronutrients Mg, S, B, Cu, Fe, Mn, Mo, Zn, and having a ratio of 15-9-12 of N—P—K (OSMO-COTE™ Plus, Everris NA Inc, Dublin, Ohio USA) was added at 65 g per pot and mixed thoroughly by hand. Sprouting potato tubers cv. 'Colomba' (obtained from H. Niven, ES Cropconsult Ltd., Richmond, BC) were cut to include at least two eyes per seed piece, placed 5-6 inches deep into the potting mix and lightly covered with the potting mix. The misting system was turned back on and timer was set to run for 2 min every 6 h beginning at 6 pm. Soil temperature at planting was 15° C. and soil moisture was approximately 20%. Shoot emergence after 2 weeks was 99%. The seed pieces were not treated with any fungicide or insecticide.

ENTONEM (*Steinernema feltiae* nematodes, Koppert Biologicals) was applied as a drench at 5000 nematodes per mL in 50 ml per pot on January 14, to control fungus gnats. No fungus gnats were present in the following weeks.

Two days before the first test product application, shoot tips were cut back by 10-15 cm to encourage bushing out and to remove any lanky or overgrown shoots. Pruners were wiped with alcohol between cuts but the cuts were allowed to air dry and were not sprayed with disinfectant. The plants were tied and staked to prevent breakage of shoots.

Applications:

The trial was laid out in a randomized complete block (RCB) design on a single greenhouse bench with 5 replicates per treatment and 2 plants per plot (10 plants per treatment). The test products were applied 5 times at weekly intervals, February 5, 12, 19, 26 and March 6 and, on each application date, the check plots were sprayed with water alone. The solution volume applied was equivalent to 1500 L/ha (300 mL/2 m$^2$). For each application, the plants in each treatment were removed from the trial bench, placed in a 2 m$^2$ area on a plastic ground sheet, sprayed with the product or water, then returned to the bench, after the product had dried. Test product applications and rates are summarized in Table 4.

TABLE 4

Treatments, rates and volume applied.

| Treatment | Rate of Product Applied | No. of Applications and Interval | Solution Volume per hectare | Solution Volume/ Treatment (per 2 m² spray-area) | Amount of Product/ Mix Volume (300 mL) |
|---|---|---|---|---|---|
| 1. Un-inoculated (Healthy) Check (water only) | — | — | 1500 L | 300 mL | — |
| 2. Inoculated Check (water only) | — | — | 1500 L | 300 mL | — |
| 3. PEG only | 2.8 g/L | 5 × 7 days | 1500 L | 300 mL | 0.56 g |
| 4. PEG-bis-BETULIN 4.0 KDa at ½ X rate | 0.8 g/L | 5 × 7 days | 1500 L | 300 mL | 0.15 g |
| 5. PEG-bis-BETULIN 4.0 KDa at 1 X rate | 1.6 g/L | 5 × 7 days | 1500 L | 300 mL | 0.32 g |
| 6. COPPER SPRAY 50W (standard label rate)* | 4.0 g/L* | 5 × 7 days | 1500 L | 300 mL | 1.2 g |
| 7. PEG-mono-BETULIN 3.5 KDa at ¼ X rate | 0.7 g/L | 5 × 7 days | 1500 L | 300 mL | 0.14 g |
| 8. PEG-mono-BETULIN 3.5 KDa at ½ X rate | 1.4 g/L | 5 × 7 days | 1500 L | 300 mL | 0.27 g |
| 9. PEG-mono-BETULIN 3.5 KDa at 1 X rate | 2.8 g/L | 5 × 7 days | 1500 L | 300 mL | 0.56 g |
| 10. PEG-mono-BETULIN 3.5 KDa at 2 X rate | 5.6 g/L | 5 × 7 days | 1500 L | 300 | 1.11 |

After each application, the trial area was covered with a clear plastic tent and the irrigation was turned off for 24 h to allow the products to dry on the leaves. After the second last application on February 26, the overhead mist was turned off and the plants were sub-irrigated only, by wetting the capillary mat with two soaker hoses, for 6 min. twice a day, at 10 a.m. and 10 p.m.

Inoculation: Inoculum of *Phytophthora infestans* (genotype US8 originally isolated from a potato crop in the BC Fraser Valley and obtained from Dr. L. Kawchuk, AAFC, Lethbridge, AB) was applied on February 13, 24 h after the second fungicide application in a total volume of 1.5 L of inoculum solution per 90 plants. The inoculum was prepared from 30, 28-day-old, V8 agar plates (200 mL clarified V8 juice, 2.0 g $CaCO_3$, 0.05 g B-cholesterol/L). Each plate was flooded with 10 mL sterile $dH_2O$ and mycelium and sporangia were gently scraped with a scalpel into a 1 L flask. This solution was poured through a #18 mesh strainer to remove mycelial clumps. The total volume of 300 mL contained $6.3 \times 10^4$ sporangia per mL (mean of 3 haemocytometer slides×2 counts each). To this was added 250 mL of a 5-day-old liquid culture in the same V8 medium that had been incubated on a shaker at 100 rpm in the dark at room temperature and contained $3 \times 10^6$ zoospores per mL by haemocytometer count. Distilled water was added to bring the final volume up to 1.5. L. The final inoculum solution contained a calculated concentration of $2.1 \times 10^4$ sporangia/mL and $5 \times 10^6$ zoospores/mL.

The plants were inoculated using a pump-action broadcast sprayer over the entire plant area. The inoculated plants were covered with black plastic for 24 h to create high humidity and low light for sporangial germination and infection of the plant tissue. The non-inoculated check plants were placed 5 m away on a separate bench for protection from the spores in the inoculation mixture, and covered with black plastic, also. After 24 h, the black plastic was removed and replaced with a clear plastic tent and the mist irrigation was turned back on. The ends of the plastic tent were left open to allow air movement and cooling on sunny days. After the first product application, the non-inoculated, water check plants were returned to the trial bench in the RBC design.

A preliminary inoculation test on potato and tomato plants showed that late blight lesions developed from either sporangia (solid plate) or zoospore (liquid culture) inoculum after 10 days under the trial conditions. Lesions were produced on both potato cv. 'Colomba' and on tomato plants in a KPU student trial on a nearby bench.

Disease Assessment:

The number of *P. infestans* lesions per plant (leaves and petioles) and the percentage of diseased leaves out of total leaves per plant was counted weekly, from one week after the first application (February 12; 24 h prior to inoculation) to one week after the last application (March 12). Disease severity was assessed using the Horsfall-Barratt grade scale of 0-11, a standard assessment scale for late blight of potato. The H-B grades were transformed to percentages following the accepted formula of Redman, King and Brown (ELANCO). The area under the disease progress curve (AUDPC) was calculated for each assessment parameter over the course of the trial where N=the number of disease assessments; t=time; y (0) is the initial infection or disease level at t=0 (i.e., when disease was first observed), $y_i$ is the disease rating on each date and the AUDPC ($A_k$) at $t=t_k$, is the total accumulated disease rating at the end of the trial:[2]

$$A_k = \sum_{i=1}^{N_i-1} \frac{(y_i + y_{i+1})}{2}(t_{i+1} - t_i)$$

Data was analyzed statistically (ANOVA) using CoStat, Version 6.400, 2008, CoHort Software, Monterey Calif., USA, ©1998-2008, and treatment means were compared in LSD, Duncan's Multiple Range Test (Duncan's MRT) and Tukey's HSD at P=0.05. LSD is the weakest statistical test, Duncan's MRT is mid-range and Tukey's is the strongest test.

Environmental conditions in the greenhouse were recorded at each application time and temperature and relative humidity were recorded hourly, throughout the trial period, using a HOBO data logger placed on the bench in the crop canopy. Environmental conditions in the greenhouse were cool and humid, with a mean temperature of 12.6-17.6° C. and a mean relative humidity of 80.9-96.7, favourable for development of late blight of potato caused by *P. infestans* (see Table 5).

TABLE 5

Mean hourly recordings: HOBO Data Logger.

| Month | Temperature (° C.) | | | Relative Humidity | | |
|---|---|---|---|---|---|---|
| | Maximum | Minimum | Mean | Maximum | Minimum | Mean |
| December 30-31 | 19.7 | 16.5 | 17.6 | 99.5 | 75.7 | 90.8 |
| January 1-31 | 27.6 | 7.3 | 16.0 | 98.5 | 48.2 | 80.9 |
| February 1-28 | 26.8 | 0.1 | 12.6 | 100 | 52.0 | 93.4 |
| March 1-12 | 32.1 | 4.2 | 14.8 | 100 | 34.2 | 96.7 |

FIG. 1 shows the disease incidence, i.e., the mean number of late blight lesions per plant per date and area under the disease progress curve (AUDPC) over the course of the trial and is summarized in Table 3.

As can be seen in Table 6, mean number of late blight lesions per plant (Table 6) there was no statistical difference between the inoculated check and the treated plants until March 5, when the treatments with PEG-bis-betulin at 0.5 and 1× rates and Copper 50W had fewer disease lesions than the inoculated check in LSD at P=0.05. On March 12, one week after the last application, plants treated with PEG bis-betulin at the 1× rate had a mean of 8.5 lesions per plant, statistically different from the check in LSD at P=0.05, while plants treated with Copper 50W had a mean of 5.5 lesions per plant, statistically different from the inoculated check in Duncan's MRT at P=0.05, but not statistically different from PEG bis-betulin at the 1× rate. Overall, in AUDPC, the plants treated with PEG-betulin at the 1× rate had 60.4% fewer late blight lesions than the inoculated check. The 0.5× rate of PEG-bis-betulin, PEG alone and the mono-betulin formulations were not statistically different from the inoculated check.

TABLE 6

Mean number of late blight lesions per plant.[1,2]

| Treatment | Product Rate | Feb 12[3] | Feb 19[3] | Feb 26[3] | Mar 5[3] | Mar 12[3] | AUDPC[3] |
|---|---|---|---|---|---|---|---|
| 1. Inoculated Check | Water Only | 0.2 ± 0.6 ab (a) | 0.2 ± 0.6 bc (ab) | 2.4 ± 1.6 abc (ab) | 14.2 ± 15.9 a (a) | 19.0 ± 12.5 a (a) | 184.8 ± 155.6 a (a) |
| 2. Non-Inoculated Check | Water Only | 0.0 ± 0.0 b (a) | 0.0 ± 0.0 c (b) | 0.0 ± 0.0 c (b) | 0.7 ± 1.4 c (b) | 5.0 ± 5.3 c (c) [a] | 22.4 ± 28.0 c (b) |
| 3. PEG only | 2.8 g/L | 0.5 ± 1.1 ab (a) | 0.7 ± 1.3 abc (ab) | 3.1 ± 3.2 ab (a) | 13.3 ± 12.7 a (a) | 18.3 ± 10.8 a (a) | 185.5 ± 130.0 a (a) |
| 4. PEG-bis-betulin 0.5X | 0.8 g/L | 0.0 ± 0.0 b (a) | 1.6 ± 3.1 abc (ab) | 2.2 ± 2.1 abc (ab) | 4.7 ± 5.2 bc (ab) | 11.4 ± 8.9 abc (abc) | 99.4 ± 70.0 abc (ab) |
| 5. PEG-bis-betulin 1X | 1.6 g/L | 0.2 ± 0.4 ab (a) | 0.6 ± 0.9 bc (ab) | 1.0 ± 1.1 bc (ab) | 4.5 ± 5.3 bc (ab) | 8.5 ± 8.7 bc (abc) | 73.2 ± 66.9 bc (ab) |
| 6. COPPER 50W | 4.0 g/L | 2.3 ± 5.6 a (a) | 2.3 ± 4.3 ab (ab) | 3.8 ± 4.5 a (a) | 4.2 ± 4.9 bc (ab) | 5.5 ± 4.3 c (bc) | 99.4 ± 126.2 abc (ab) |
| 7. PEG-mono-betulin 0.25X | 0.7 g/L | 0.5 ± 0.8 ab (a) | 0.7 ± 0.9 abc (ab) | 2.5 ± 1.9 abc (ab) | 9.9 ± 8.4 ab (ab) | 15.9 ± 12.9 ab (ab) | 149.1 ± 102.9 ab (a) |
| 8. PEG-mono-betulin 0.5X | 1.4 g/L | 1.4 ± 2.4 ab (a) | 1.9 ± 2.6 abc (ab) | 3.4 ± 4.2 ab (a) | 11.4 ± 13.8 ab (a) | 12.7 ± 17.0 abc (abc) | 166.2 ± 198.0 ab (a) |
| 9. PEG-mono-betulin 1X | 2.8 g/L | 0.2 ± 0.6 ab (a) | 1.1 ± 2.3 abc (ab) | 3.1 ± 4.1 ab (a) | 7.7 ± 9.1 abc (ab) | 13.7 ± 9.1 abc (abc) | 132.0 ± 115.1 ab (ab) |
| 10. PEG-mono-betulin 2X | 5.6 g/L | 2.1 ± 4.3 ab (a) | 2.9 ± 4.9 a (a) | 3.8 ± 4.5 a (a) | 10.4 ± 10.1 ab (ab) | 14.1 ± 9.1 abc (abc) | 176.4 ± 158.3 ab (a) |

[1]Mean and standard deviation of two plants per plot, 5 replicates per treatment, RCB design.
[2]Treatments applied Feb. 5, Feb. 12, Feb. 19, Feb. 26 and March 5.
[3]Numbers in the same column followed by the same letter are not significantly different in LSD and (Duncan's MRT) in brackets at P = 0.05. No differences were found in Tukey's HSD at P = 0.05.

Figure 2:
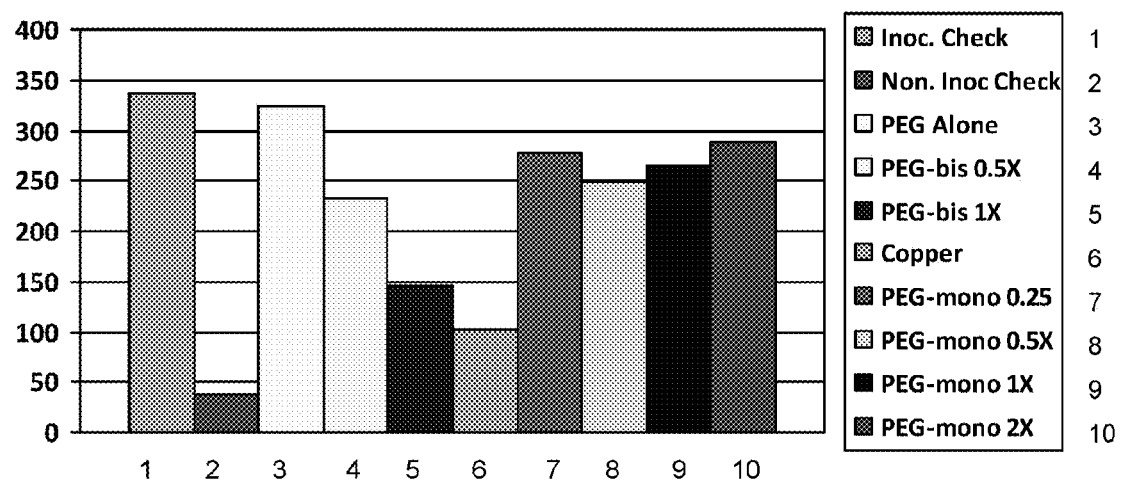
FIG. 2 is a graph showing the mean percentage of diseased leaves per plant (AUPDC).

FIG. 2 (and Table 7) show the mean percentage of diseased leaves and AUDPC. On March 5, both of the PEG-bis-betulin treatments, had a significantly lower percentage of diseased leaves than the inoculated check, different in Duncan's MRT at P=0.05, and were similar to the commercial fungicide, COPPER 50W (Table 7). Over all of the trial, the plants treated with PEG bis-betulin at the 1× rate had 57% fewer diseased leaves than the inoculated check, significantly different in Duncan's at P=0.05 and not statistically different from COPPER 50W (Table 7).

TABLE 7

Mean percentage of diseased leaves per plant.[1,2]

| Treatment | Product Rate | Feb 12[3] | Feb 19[3] | Feb 26[3] | Mar 5[3] | Mar 12[3] | AUDPC[3] |
|---|---|---|---|---|---|---|---|
| 1. Inoculated Check | Water Only | 1.1 ± 3.5 ab | 1.0 ± 3.0 ab | 8.8 ± 6.7 a | 21.6 ± 26.0 a (a) | 32.4 ± 24.6 a (a) | 337.7 ± 284.2 a (a) |
| 2. Non-Inoculated Check | Water Only | 0.0 ± 0.0 b | 0.0 ± 0.0 b | 0.0 ± 0.0 b | 1.0 ± 2.0 e (c) | 9.1 ± 7.4 bc (a) | 38.7 ± 38.3 d (b) |
| 3. PEG only | 2.8 g/L | 3.2 ± 8.0 ab | 2.8 ± 5.2 ab | 6.9 ± 8.3 a | 19.4 ± 14.5 ab (ab) | 30.9 ± 17.6 ab (a) | 324.9 ± 160.6 a (a) |
| 4. PEG-bis-betulin 0.5X | 0.8 g/L | 0.0 ± 0.0 b | 7.8 ± 15.7 a | 6.9 ± 6.1 a | 8.2 ± 5.6 bcde (abc) | 20.8 ± 17.1 abc (a) | 232.9 ± 153.4 abc (ab) |
| 5. PEG-bis-betulin 1X | 1.6 g/L | 1.2 ± 2.5 ab | 2.2 ± 3.2 ab | 3.5 ± 3.6 ab | 5.5 ± 5.3 cde (abc) | 17.9 ± 26.6 abc (a) | 145.3 ± 140.3 bcd (ab) |
| 6. COPPER 50W | 4.0 g/L | 2.1 ± 3.4 ab | 2.2 ± 3.2 ab | 4.1 ± 3.6 ab | 4.5 ± 3.8 de (bc) | 5.9 ± 2.7 c (a) | 103.5 ± 78.4 cd (ab) |
| 7. PEG-mono-betulin 0.25X | 0.7 g/L | 2.5 ± 4.3 ab | 2.1 ± 2.9 ab | 6.2 ± 3.3 a | 16.0 ± 10.0 abc (abc) | 28.1 ± 28.9 ab (a) | 277.8 ± 144.0 ab (ab) |
| 8. PEG-mono-betulin 0.5X | 1.4 g/L | 4.8 ± 5.5 ab | 6.3 ± 4.8 ab | 8.4 ± 5.3 a | 11.2 ± 8.5 abcde (abc) | 14.1 ± 14.9 abc (a) | 248.9 ± 153.6 abc (ab) |
| 9. PEG-mono-betulin 1X | 2.8 g/L | 1.4 ± 4.5 ab | 3.2 ± 7.5 ab | 7.1 ± 7.0 a | 10.8 ± 9.5 abcde (abc) | 32.1 ± 38.0 abc (a) | 265.3 ± 242.4 abc (ab) |
| 10. PEG-mono-betulin 2X | 5.6 g/L | 5.4 ± 10.3 a | 5.8 ± 7.7 ab | 7.7 ± 6.2 a | 15.2 ± 6.7 abcd (abc) | 19.7 ± 8.9 abc (a) | 289.1 ± 187.9 ab (a) |

[1]Mean and standard deviation of two plants per plot, 5 replicates per treatment, RCB design.
[2]Treatments applied Feb. 5, Feb. 12, Feb. 19, Feb. 26 and March 5.
[3]Numbers in the same column followed by the same letter are not significantly different in Duncan's MRT and (Tukey's HSD) in brackets at P = 0.05.

Figure 3:
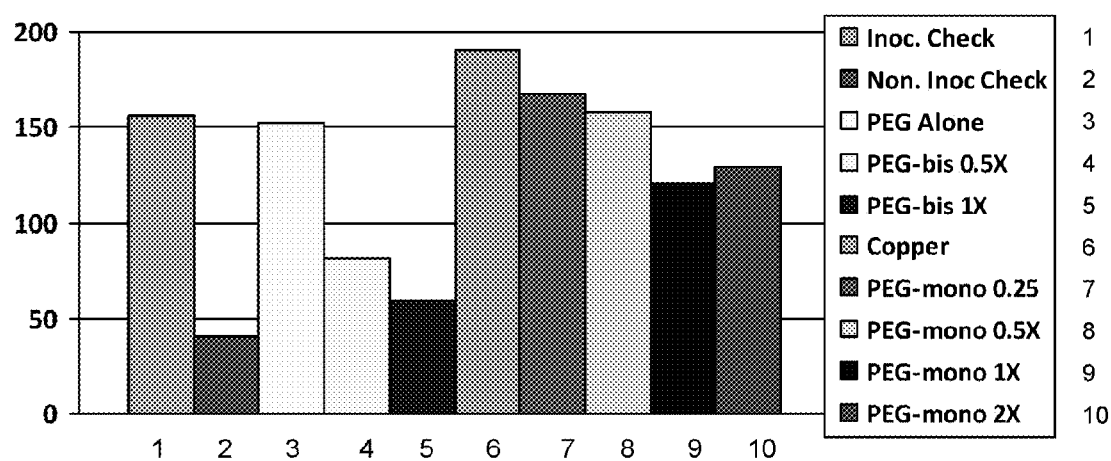
FIG. 3 is a graph showing the mean percentage of leaf area diseased per plant (AUDPC).

Disease severity, i.e., the mean percent leaf diseased per plant and AUDPC is shown in Table 8 and FIG. 3. On March 12, the plants treated with PEG-bis-betulin at the 1× rate also had the lowest percentage of leaf area diseased (except for the non-inoculated (healthy) check) (Table 8).

TABLE 8

Mean percentage of leaf area diseased per plant
(rated on the H-B scale transformed to percentages).[1,2]

| Treatment | Product Rate | Feb 12[3] | Feb 19[3] | Feb 26[3] | Mar 5[3] | Mar 12[3] | AUDPC[3] |
|---|---|---|---|---|---|---|---|
| 1. Inoculated Check | Water Only | 1.2 ± 0.3 b | 1.2 ± 0.3 b | 3.4 ± 2.4 b | 5.8 ± 4.9 a (a) | 22.1 ± 23.8 a (a) | 155.9 ± 128.9 abc (a) |
| 2. Non-Inoculated Check | Water Only | 1.2 ± 0.0 b | 1.2 ± 0.0 b | 1.2 ± 0.0 b | 1.4 ± 0.4 c (a) | 2.8 ± 0.9 d (b) | 40.1 ± 6.9 c (a) |
| 3. PEG only | 2.8 g/L | 1.4 ± 0.5 b | 1.8 ± 1.1 b | 3.6 ± 3.2 b | 7.4 ± 6.5 a (a) | 16.1 ± 12.8 abc (ab) | 151.7 ± 98.2 abc (a) |
| 4. PEG-bis-betulin 0.5X | 0.8 g/L | 1.1 ± 0.0 b | 1.5 ± 0.5 b | 2.4 ± 0.9 b | 2.2 ± 0.3 a (a) | 9.6 ± 10.1 bcd (ab) | 81.1 ± 36.5 abc (a) |

TABLE 8-continued

Mean percentage of leaf area diseased per plant
(rated on the H-B scale transformed to percentages).[1,2]

| Treatment | Product Rate | Feb 12[3] | Feb 19[3] | Feb 26[3] | Mar 5[3] | Mar 12[3] | AUDPC[3] |
|---|---|---|---|---|---|---|---|
| 5. PEG-bis-betulin 1X | 1.6 g/L | 1.4 ± 0.5 b | 1.6 ± 0.6 b | 1.8 ± 0.6 b | 2.1 ± 1.0 a (a) | 4.3 ± 2.9 cd (b) | 59.4 ± 17.2 bc (a) |
| 6. COPPER 50W | 4.0 g/L | 3.4 ± 5.5 a | 6.1 ± 11.3 a | 8.1 ± 11.7 a | 8.3 ± 11.6 a (a) | 5.9 ± 5.3 cd (ab) | 190.2 ± 264.9 a (a) |
| 7. PEG-mono-betulin 0.25X | 0.7 g/L | 1.5 ± 0.56 b | 1.6 ± 0.6 b | 3.6 ± 2.4 b | 7.8 ± 5.0 a (a) | 20.0 ± 13.7 ab (ab) | 167.2 ± 76.0 ab (a) |
| 8. PEG-mono-betulin 0.5X | 1.4 g/L | 2.0 ± 1.1 ab | 2.3 ± 1.0 b | 3.5 ± 2.3 b | 7.9 ± 7.5 a (a) | 15.4 ± 16.0 abc (ab) | 157.8 ± 122.0 abc (a) |
| 9. PEG-mono-betulin 1X | 2.8 g/L | 1.5 ± 1.10 b | 1.4 ± 0.5 b | 3.7 ± 5.3 b | 6.5 ± 10.9 a (a) | 9.6 ± 10.1 bcd (ab) | 120.9 ± 147.8 abc (a) |
| 10. PEG-mono-betulin 2X | 5.6 g/L | 2.0 ± 1.5 ab | 2.3 ± 1.4 b | 2.7 ± 1.1 b | 8.1 ± 10.6 a (a) | 8.4 ± 6.0 bcd (ab) | 129.1 ± 83.1 abc (a) |

[1]Mean and standard deviation of two plants per plot, 5 replicates per treatment, RCB design.
[2]Treatments applied Feb. 5, Feb. 12, Feb. 19, Feb. 26 and March 5.
[3]Numbers in the same column followed by the same letter are not significantly different in Duncan's MRT and (Tukey's HSD) in brackets at P = 0.05.

The mean percentage of diseased leaf are per plant was equivalent in plants treated with PEG-bis-betulin 1× and plants treated with COPPER 50W and the only treatment statistically different from the inoculated check in Tukey's HSD at P=0.5. Overall, the AUDPC for leaf area diseased was 62% less than the inoculated check and statistically lower than copper. On March 12, the highest rates (1× and 2×) of PEG-mono-betulin were statistically better than the control also, i.e., had smaller disease lesions than the water control, and were statistically similar to the commercial fungicide treatment, but not in overall AUDPC.

Figure 4:
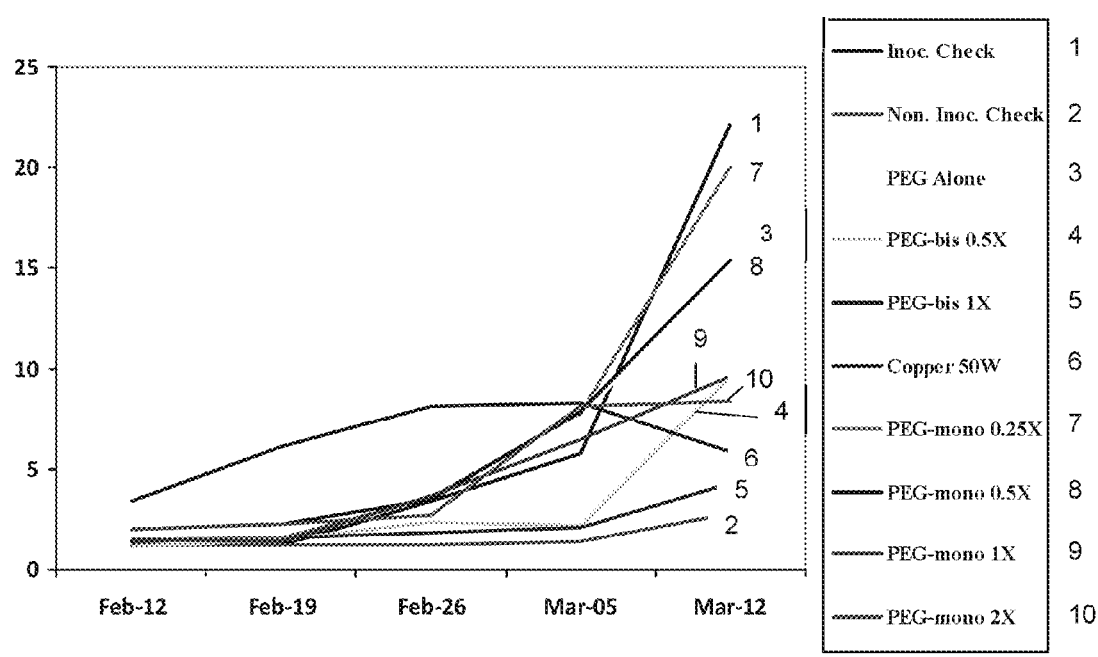
FIG. 4 is a graph showing the mean percentage of leaf area diseased per plant per week.

FIG. 4 shows the mean percentage of leaf area diseased each week of the trial (rated on the H-B scale transformed to percentages). A few disease lesions appeared naturally on the plants prior to inoculation on February 13; possibly from a student experiment inoculated the previous week. The non-inoculated plants remained disease-free until March 5, which confirmed that the disease was actively spreading among the treated plants under the plastic tent. Disease lesions increased greatly in size in the last week (percent leaf area diseased). No phytotoxicity was observed in any treatment.

Conclusions:

In a replicated, randomized greenhouse experiment, on potato cv. 'Colomba' inoculated with a US8 strain of *Phytophthora infestans*, weekly foliar sprays of PEG bis-betulin at the 1× rate (1.6 g/L) suppressed late blight of potato as well as, or better than, the registered fungicide Copper 50W (copper oxychloride) at the label rate (4 g/L). This PEG bis-betulin treatment reduced the number of disease lesions by 60%, the number of infected leaves by 57% and leaf area affected by 62% compared to the inoculated control, in AUDPC. The 0.5× dilution of the PEG-bis betulin product gave some disease suppression, but was statistically ineffective.

The PEG-mono-betulin formulation gave only slight disease suppression and was not statistically effective at any concentration, from 0.25× to 2× (0.7-5.6 g/L). However, at the 1× rate, PEG mono-betulin reduced the number of disease lesions by 28.6%, the number of infected leaves by 21.4% and leaf area affected by 22.5% compared to the inoculated control, in AUDPC. PEG alone had no effect on disease pressure.

The greenhouse plants were irrigated by overhead irrigation twice daily for the first 3 weeks of the trial and only sub-irrigated for the final two weeks. Irrigation did not appear to affect disease development or product performance, except for the standard fungicide, COPPER 50W, which performed better without overhead irrigation. One of the limitations of copper fungicide is that it is easily dissolved in water and washes off of the leaves under rain or irrigation. No phytotoxicity was observed in any treatment.

Without being bound by theory, these results indicate the combination of high lipid solubility and low water solubility of PEG Bis Betulin Ester compared to PEG mono betulin may be responsible for its increased antifungal activity, as compared to PEG mono betulin.

Example 6

PEG-Bis-Betulin was Tested for Control of *Fusarium* Patch (Pink Mould) of Turfgrass Caused by *Microdochium nivale* in Fall/Winter.

An aqueous solution of PEG bis-Betulin Ester, as prepared in Example 3 was also tested for use as an antifungal agent against Microdochium patch (pink snow mould) on golf green turf grass. On a commercial golf green, PEG bis-betulin formulated at a 1× rate suppressed the disease as well as the registered fungicides BANNER MAXX (propiconazole) or COMPASS 50WG (trifloxystrobin) at their lowest label rates. Three applications of PEG bis-betulin in the fall reduced the number of disease spots by 57% and the percent turf area diseased by 70% compared to the control, in February of the following year. The 0.5× dilution of the PEG-betulin product was ineffective. A 2× application of the product, i.e., twice the solution volume, increased the incidence and severity of the disease somewhat compared to the 1× rate, although there were no visible symptoms of phytotoxicity.

PEG bis-Betulin was found to be significantly different from the water control for all parameters tested and not statistically different when compared to the standard commercial fungicides, BANNER MAXX and COMPASS 50 WG. There was, however, no significant difference in disease levels among the rates of PEG-betulin applied.

Example 7

PEG-Bis-Betulin was Tested for Control of *Botrytis* of Bean in a Greenhouse Crop in Winter.

A solution of PEG-bis-Betulin Ester 4,000 Da (1.7 g/L) in water, as prepared in EXAMPLE 3 was applied preventatively as a foliar spray 24 hours before inoculation of bean leaves with a known fungal pathogen, *Botrytis cinerea*. This application reduced the number of *Botrytis* lesions on bean leaves for up to 14 days and performed as well as the standard *botrytis* fungicide, SWITCH 62.5 WDG (cyprodinil+fludioxonil). The number of lesions was 50% less than on the inoculated check plants and the maximum lesion size was also significantly reduced. The percent leaf area diseased was 90.7% less than the inoculated check after 14 days, compared to 63.5% for plants treated with SWITCH fungicide. No phytotoxicity was observed in any treatment.

When applied three days post-inoculation, as a "curative" spray to treat infected plants, PEG bis-Betulin Ester appeared to stop lesion expansion: the mean number and maximum diameter of *botrytis* lesions in the PEG-betulin "curative" treatment were statistically less than in the inoculated check for up to 7 days after inoculation. The percent leaf area diseased was 81.4% less than the check at 14 days. No phytotoxicity was observed in any treatment.

PEG-bis-betulin at a concentration of 1.7 g/L showed both protectant activity when applied 24-48 hours pre-inoculation and curative activity when applied 72 hours post-inoculation.

In other testing, systemic activity was observed, in that upper leaves developed fewer and smaller lesions when PEG-betulin was applied to the lower leaves only. This may be due to induction of natural plant defense mechanisms (SAR) or translocation of the product systemically within the plant. However, disease control with the product "in planta" was achieved at a 1/5 dilution of the effective rate on *Botrytis cinerea* "in vitro", which suggests a possible stimulation of the plant's own defense mechanisms (SAR) in addition to a direct effect on the pathogen. No phytotoxicity was observed.

Without being bound to theory, it is presumed that this water soluble form of betulin is readily absorbed by the leaves of the test plant. Once absorbed, the ester bond of the PEG bis-betulin ester prodrug may be hydrolyzed chemically or enzymatically, resulting in the release of betulin. After separation from the PEG carrier, betulin may then be free to function as an antifungal agent.

Example 8

Laboratory Tests In-Vitro: *Botrytis cinerea*

PEG-bis-betulin as prepared in EXAMPLE 3 inhibited fungal mycelial growth in vitro. When *Botrytis cinerea* and nutrients for fungal growth were added to the liquid formulation of PEG-bis-betulin at the 1× rate, no difference was found in the number of *Botrytis* colonies plated after 48 hours, but, after 7 days, a 77.9% reduction in fungal weight (*Botrytis* mycelial growth) was recorded as compared to the water check. PEG-bis-betulin at a 50 or 75% dilution was not different from the water check.

The above-described embodiments are intended to be examples only. Alterations, modifications and variations can be effected to the particular embodiments by those of skill in the art. The scope of the claims should not be limited by the particular embodiments set forth herein, but should be construed in a manner consistent with the specification as a whole. The contents of all references and published patent applications cited throughout this application are hereby incorporated by reference.

What is claimed is:

1. A PEGylated bis pentacyclic triterpene having the formula:

A---P---B, wherein,
A is a first pentacyclic triterpene;
B is a second pentacyclic triterpene; and
P is a polyethylene glycol (PEG) molecule with an average molecular weight of from about 400 daltons (Da) to about 8000 Da, for use in treating a fungal disease in a plant, wherein the fungal disease is blight;
said first and second pentacyclic triterpenes are each independently betulin, betulinic acid, or lupeol; and
A and B are each independently covalently bound to P by an ester linkage at C3 or C28.

2. The PEGylated bis pentacyclic triterpene of claim 1, wherein the first and second pentacyclic triterpenes are each betulin.

3. The PEGylated bis pentacyclic triterpene of claim 1, wherein the PEG molecule has a molecular weight of about 1500 Da to about 8,000 Da.

4. The PEGylated bis pentacyclic triterpene of claim 3, wherein the PEG molecule has a molecular weight of about 3,000 Da.

5. The PEGylated bis pentacyclic triterpene of claim 1, wherein the PEG molecule is α,ω biscarboxymethyl PEG.

6. The PEGylated bis pentacyclic triterpene according to claim 1, wherein the first and second pentacyclic triterpenes are each betulin, the PEG molecule has a molecular weight of about 1500 Da to about 8,000 Da, and the blight is
caused by a fungal pathogen selected from the group consisting of *Phytophthora infestans, Microdochium nivale*, and *Botrytis cinerea*.

7. A fungicidal composition comprising the PEGylated bis pentacyclic triterpene as defined in claim 1; and an agriculturally acceptable diluent, for treating blight in plants.

8. A method of treating a fungal disease in a plant, wherein the fungal disease is blight, said method comprising:
applying to the plant, to a soil supporting the plant, or to both the plant and the soil supporting the plant, a composition comprising:
a PEGylated bis pentacyclic triterpene having the formula:

A---P---B, wherein,
A is a first pentacyclic triterpene;
B is a second pentacyclic triterpene; and
P is a polyethylene glycol (PEG) molecule with an average molecular weight of from about 400 daltons (Da) to about 8000 Da; and
an agriculturally acceptable diluent;
wherein the first and second pentacyclic triterpenes are each independently betulin, betulinic acid, or lupeol; and wherein A and B are each independently linked to P by an ester linkage at C3 or C28.

9. The method of claim 8, wherein the composition is applied to the leaves of the plant.

10. The method of claim 8, wherein the first and second pentacyclic triterpene are each betulin.

11. The method of claim 8, wherein the PEG molecule has a molecular weight of about 1500 Da to about 8,000 Da.

12. The method of claim 11, wherein the PEG molecule has a molecular weight of about 3,000 Da.

13. The method of claim 8, wherein the PEG molecule is α,ω biscarboxymethyl PEG.

14. The method of treating a fungal disease in a plant according to claim 8, wherein the first and second pentacyclic triterpenes are each betulin, the PEG molecule has a molecular weight of about 1500 Da to about 8,000 Da, and the blight is caused by a fungal pathogen selected from the group consisting of *Phytophthora infestans, Microdochium nivale*, and *Botrytis cinerea*.

\* \* \* \* \*